United States Patent [19]

Bonati et al.

[11] 4,166,861
[45] Sep. 4, 1979

[54] PHARMACOLOGICALLY ACTIVE POLYPHENOLIC SUBSTANCES

[75] Inventors: Attilio Bonati; Giuseppe Mustich, both of Milan, Italy

[73] Assignee: Inverni della Beffa S.p.A., Milan, Italy

[21] Appl. No.: 780,171

[22] Filed: Mar. 22, 1977

[30] Foreign Application Priority Data

Mar. 23, 1976 [GB] United Kingdom ............... 11666/76

[51] Int. Cl.² ........................................... A61K 31/335
[52] U.S. Cl. ................... 424/278; 260/345.5; 260/340.5 R; 546/256; 424/266; 546/270; 546/269
[58] Field of Search ...................... 424/278; 260/345.5

[56] References Cited

U.S. PATENT DOCUMENTS 3,546,250  12/1970  Krämer et al. ............... 260/345.5 X

FOREIGN PATENT DOCUMENTS

| 7941M | 5/1970 | France | 424/278 |
| 2073251 | 10/1971 | France | 424/278 |
| 2128207 | 10/1972 | France | 424/278 |
| 598907 | 10/1959 | Italy | 260/345.5 |
| 1057349 | 2/1967 | United Kingdom | 260/345.5 |

OTHER PUBLICATIONS

Vitaminy, Akademiya Nauk Ukrainskoi SSR., Inst. Biokhimii, vol. 3, 1958, pp. 50-59.

*Primary Examiner*—Ethel G. Love
*Attorney, Agent, or Firm*—Browdy and Neimark

[57] ABSTRACT

The pharmacological activity of epicatechin and of certain novel esters and ketals of catechin and of epicatechin is described. The use of said compounds in order to ellicit a choleretic, hypocholesterolimic, hypolipaemic or hepatoprotective effect is described along with pharmaceutical compositions for use in these treatments.

10 Claims, No Drawings

PHARMACOLOGICALLY ACTIVE POLYPHENOLIC SUBSTANCES

This invention relates to pharmacologically active polyphenolic substances and to processes for their production.

Catechin (I) and epicatechin (II) are polyphenolic substances which are widely distributed in nature

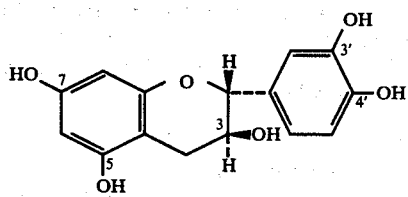

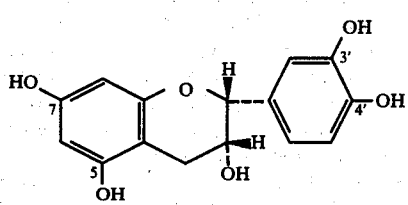

We have now found that epicatechin and certain novel derivatives of catechin and of epicatechin possess remarkable choleretic, hypocholesterolemic, hypolipaemic and hepatoprotective activity and are of relatively low toxicity.

Thus according to one aspect of the present invention, there are provided pharmaceutical compositions comprising epicatechin and/or one or more pharmaceutically acceptable ketals or esters of catechin or of epicatechin and a pharmaceutically acceptable diluent or carrier.

The esters and ketals of catechin and epicatechin may have the general formulae III or IV

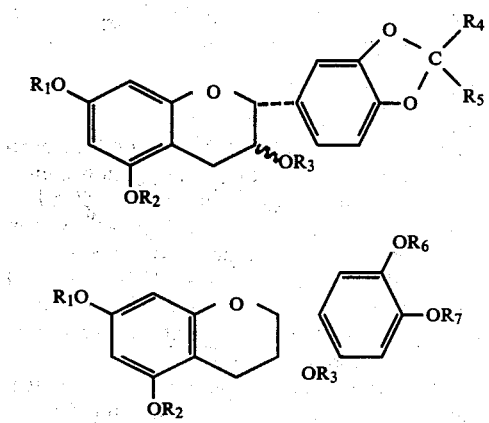

wherein in formula III $R_1$, $R_2$ and $R_3$ each represent a hydrogen atom or an acyl group and $R_4$ and $R_5$ each represent a lower alkyl group (as hereafter defined), and in formula IV, at least one of $R_1$, $R_2$, $R_3$, $R_6$ and $R_7$ represents an acyl group and each of the others represents an acyl group or a hydrogen atom, and such esters and ketals form a further aspect of the present invention.

It will be appreciated that where a compound of formula III or IV is a derivative of catechin, the group —$OR_3$ will be in the β-configuration and where the compound is a derivative of epicatechin, the group —$OR_3$ will be in the α-configuration.

The acyl radicals represented by $R_1$, $R_2$, $R_3$, $R_6$ and $R_7$ may be derived from acids of the formula RCOOH where R is an alkyl or substituted alkyl group, aryl or substituted aryl group, aralkyl or substituted aralkyl group, aralkenyl or substituted aralkenyl groups or heterocyclic group.

Although the upper molecular weight of the acid RCOOH is not unduly critical, generally the acid should not contain more than 20 and preferably not more than 15 carbon atoms. Thus it is preferred that the substituted or unsubstituted alkyl groups represented by R should be substituted or unsubstituted lower alkyl groups by which are meant alkyl groups containing 1 to 8 carbon atoms, e.g. methyl, ethyl, propyl, butyl, pentyl, hexyl, heptyl and octyl, and such groups may be straight chained as in n-butyl, branched as in iso-propyl or cyclic as in cyclohexyl. Also it is preferred that the alkyl and alkenyl constituents of the substituted and unsubstituted aralkyl and aralkenyl groups should be derived from lower alkyl and lower alkenyl groups wherein the term "lower" is as defined above.

The aryl groups represented by R and also the aryl constituents of the aralkyl and arakenyl groups are preferably phenyl. These aryl groups may themselves be substituted by one or more alkyl groups as defined above.

Heterocyclic groups represented by R may, for example, be nitrogen-containing heterocyclic groups, such as pyridyl.

Examples of possible substituents on the R group of the carboxylic acids RCOOH include halogen, hydroxy, alkoxy (and preferably lower alkoxy groups derived from the lower alkyl groups defined above), and esterified hydroxy, particularly hydroxy esterified with an acid $R^1COOH$ wherein $R^1$ is lower alkyl as defined above.

A particularly preferred class of compounds according to the invention are those in which one or more of the acyl radicals represented by $R_1$, $R_2$, $R_3$, $R_6$ and $R_7$ are derived from acids which in free or esterified form possess choleretic, hypocholesterolemic or hypolipaemic activity. Examples of such acids are nicotinic acid, caffeic acid, acetylferulic acid and 2-(p-chlorophenoxy)-2-methyl propionic acid.

The compounds of formulae III and IV which are esters may be prepared according to a further aspect of the invention by reacting catechin, epicatechin or a ketal of catechin or of epicatechin with an appropriate acylating agent, for example an acid anhydride or acyl chloride, preferably in the presence of a polar aprotic solvent such as, for example, pyridine or dioxan. The reaction may be carried out at room temperature or higher, according to the reactivity of the acylating agent.

According to a further aspect of the invention, compounds of formula III may be prepared from catechin, from epicatechin, or from a compound of formula IV in which $R_6$ and $R_7$ are hydrogen by reaction with a ketone in the presence of an acid catalyst.

As indicated above, the present invention includes pharmaceutical compositions comprising epicatechin and/or one or more pharmaceutically acceptable ketals or esters of catechin or of epicatechin and a pharmaceutically acceptable carrier. The invention also provides methods for producing such compositions which comprise bringing the afore-mentioned active ingredients into a form suitable for administration, for example by mixing with a pharmaceutically acceptable excipient.

The particular galenic form of the compositions of the invention depends on the intended route of administration and such forms may be amorphous or in the form of shaped dosage units. Examples include sterile liquids suitable for parenteral administration and forms suitable for oral administration (e.g. tablets, capsules, comfits, solutions or suspensions).

In formulating compositions according to the invention, a wide range of excipients may be used, the nature of which will depend, of course, on the intended mode of application of the composition. Examples include preservatives and buffering, thickening, suspending, stabilising, wetting, emulsifying, colouring and flavouring agents. Specific examples of suitable excipients include carboxy vinyl polymers, propylene glycol, ethyl alcohol, water, cetyl alcohol, saturated vegetable triglycerides, fatty acid esters or propylene glycol, triethanolamine, glycerol, starch, lactose, sucrose, cellulose sorbitol, bentonite, cellulose, methylcellulose, carboxymethyl cellulose, lauryl-sulphate, dicalcium phosphate, powdered silica, titanium dioxide, lecithin, magnesium carbonate, magnesium stearate etc.

The isolation of epicatechin and the preparation of compounds according to the present invention will now be described in more detail in the following Examples.

EXAMPLE 1

Isolation of epicatechin 35 kg. of bark of *Aesculus hippocastanum L.* were extracted several times with 80 liters of 50% alcohol in water. From the combined hydro-alcoholic extracts the organic solvent was eliminated at reduced pressure. The concentrate was then extracted repeatedly with ethyl acetate and the combined organic phases concentrated under reduced pressure to a volume of approximately 20 liters. The concentrate was then poured into 100 liters of hexane with vigorous mechanical agitation.

After filtration and drying, 1.2 kg. of raw catechins were obtained which, by repeated crystallisation from alcohol, yielded 130 g. of pure epicatechin.

M.p.=236°–238° C. with decomposition
$[\alpha]Hg = -69°$ (7 percent in ethanol).

EXAMPLE 2

Acetonides of epicatechin 6 g. of epicatechin were dissolved in 50 ml. of acetone with agitation at a temperature of 0° C. Gaseous hydrogen chloride was bubbled through the solution for 1 minute and finally the reaction mixture was poured into 500 ml. of 5% solution of sodium bicarbonate and extracted repeatedly with 100 ml. of ethyl acetate.

The combined organic phases were concentrated to 50 ml. and poured into 5 voumes of chloroform. After the precipitate had been filtered and dried, 3.8 g. of acetonides were obtained in the form of white amorphous powder. (Found: C, 65.50; H, 5.32; $C_{18}H_{18}O_6$ requires: C, 65.45; H, 5.45).

EXAMPLE 3

Triacetate of catechin acetonide 5 g. of catechin acetonide were dissolved in 25 ml. of pyridine and 25 ml. of acetic anhydride added to the solution which was then left to react overnight at room temperature. The reaction mixture was subsequently poured with mechanical agitation into 500 ml. of water at 4°–5° C. The obtained precipitate was filtered and washed with water to neutrality. On crystallisation from a mixture of isopropanol and water, 5 g. of triacetate of catechin acetonide were obtained. The product melted at 120°–122° C. (Found: C, 63.12; H, 5.30; $C_{24}H_{24}O_9$ requires: C, 63.16; H, 5.26).

EXAMPLE 4

Catechin pentaacetate

The reaction was carried out in the manner described in Example 3, but starting from 5 g. of catechin, 5 g. Of catechin pentacetate were obtained, melting at 131°–132° C. (Found: C, 59.87; H, 4,82; $C_{25}H_{24}O_{11}$ requires: C, 60; H, 4.8).

EXAMPLE 5

Epicatechin pentanicotinate 2.5 g. of epicatechin were dissolved in 25 ml. of pyridine and 25 g. of nicotinic anhydride dissolved in 100 ml. of pyridine added to the solution. The solution was heated with agitation in a thermostatically-controlled bath at 100° C. for 12 hours. The reaction mixture was then concentrated in vacuo to dryness and the residue purified by means of repeated precipitation in an acetone/hexane mixture. 5.2 g. of epicatechin pentanicotinate were obtained. (Found: C, 66.22; H, 3.48; N, 8.52; $C_{45}H_{29}N_5O_{11}$ requires: C, 66.26; H, 3.56; N, 8.59).

EXAMPLE 6

Catechin pentacaffeate 1.8 g. of catechin were dissolved in 30 ml. of dioxan. This solution was poured into a suspension of 6 g. thionyl caffeic acid chloride in 20 ml. of pyridine. The mixture was left to react overnight at room temperature and was then poured with agitation into 500 ml. of water at 4°–5° C.

The whole product was then extracted repeatedly with chloroform and the combined organic phases washed in a counter-current fashion with cold water to neutrality. After evaporation to dryness, 5 g. of an amorphous product were obtained. (Found: C, 65.39; H, 3.9; $C_{60}H_{44}O_{21}$ requires: C, 65.45; H, 4).

EXAMPLE 7

Penta-acetylferulate of epicatechin 5 g. of epicatechin were dissolved in 30 ml. of pyridine and the solution poured into a suspension constituted by 30 g. of acetylferulic acid chloride in 100 ml. of pyridine. The mixture was left to react for 48 hours at room temperature and then poured with mechanical agitation into 1,000 ml. of water at 4°–5° C. The product was repeatedly extracted with chloroform and the combined organic phases washed in a counter-current manner to neutrality with water at 4°–5° C.

The residue was then taken up with 100 ml. of acetone and the filtrate poured with agitation into 500 ml. of hexane. After filtration of the precipitate and drying, 13 g. of epicatechin penta-acetylferulate, amorphous white powder, were obtained. (Found: C, 65.15; H, 4.69; $C_{75}H_{64}O_{26}$ requires: C, 65.22; H, 4.64).

EXAMPLE 8

Catechin penta 2-(p-chlorophenoxy)-2-methyl propionate 5.2 g. of catechin were dissolved in 30 ml. of dioxan and the solution poured into a suspension of 25 g. of 2-(p-chlorophenoxy)-2-methyl propionic acid chloride in 100 ml. of pyridine. The mixture was left to react overnight at 40° C. and then poured, with agitation into 800 ml. of water at 4°–5° C. Repeated extractions were effected with chloroform and the organic phases washed in a counter-current manner with water at 4°–5° C. to neutrality and then concentrated to dryness. 12 g. of amorphous white powder were obtained.

(Found: C, 69.3; H, 5.12; Cl, 3.16; $C_{65}H_{59}ClO_{16}$ requires: C, 69; H, 5.22; Cl, 3.14).

The pharmacological activity of compounds according to the present invention are illustrated by the following tests:

A. Choleretic activity

The choleretic activity was determined in accordance with the technique described by R. Lambert in "Surgery of the Digestive System in the Rat" 1965. Sprague Dawley rats of mean weight of 230 g. were used. The products were injected intraperitoneally at the dosage of 100 mg/kg., the volume of the bile and the corresponding dry residue being measured then from 1 hour to 4 hours after administration. Epicatechin and catechin peracetylferulate were found to increase the volume of the bile by 38% and 64% respectively and increase the dry residue of the bile by 35% and 36% respectively, in comparison with the basal values. These increases are significant.

B. Activity upon the lipidic metabolism

1. Hyperlipaemic activity from olive oil

The hyperlipaemic activity was determined in 30 Sprague Dawley rats of mean weight of 160 g., in which hyperlipaemia was induced by means of administration of 20 ml/kg. of olive oil orally in animals which had been fasting for 16 hours. Two treatments were effected with the products under examination (upon groups of 18 animals), the first two hours before the olive oil, the second two hours afterwards. The doses were administered orally and were equal to 100 mg/kg. The rats were slaughtered two hours after the final treatment and the triglycerides in the plasma were measured by the colorimetric method of SIGMA CHEM Co. It was found that epicatechin and pernicotinylcatechin significantly diminished the concentration of the triglycerides in the plasma by 42% and 27% respectively in comparison with the controls.

2. Triton hyperlipaemia

Hyperlipaemia was induced by endovenous administration of 225 mg/kg. of Triton WR 1339 dissolved in physiological solution to Sprague Dawley rats of mean weight of 200 g. which had been fasting for 24 hours.

The products under examination were injected intraperitoneally at the dosage of 100 mg/kg. of which 50 mg/kg. immediately after the Triton and 50 mg/kg. after 4 hours. After a further 4 hours the animals were slaughtered and the cholesterol and triglycerides in the plasma were measured.

It was found that pernicotinylcatechin and peracetylcatechin significantly diminish the concentration of cholesterol by 21.1% and 16.3% respectively and that of the triglycerides by 28.7% and 23.1% respectively, in comparison with the controls.

3. Lipidic metabolism in the normally fed rat

The tests were conducted on Sprague Dawley rats of mean weight of 200 g. which were normolipaemic and to which the products had been administered intraperitoneally in a single dose of 100 mg/kg. After two hours the animals were slaughtered and the free fatty acids in the plasma were measured. We found that catechin acetonide and pernicotinylcatechin significantly diminish the concentration of the free fatty acids respectively by 25.8% and 13.1% in comparison with the controls.

C. Comparison of Choleretic and Hypolipaemic Activity of Compounds According to the Invention and Catechin 1. Choleretic Activity—Oral Administration The choleretic activities of catechin and epicatechin were determined in the manner described in paragraph A above except that the substances under test were administered per os at the rate of 200 mg/kg.

From the results shown in Table 1 it can be seen that epicatechin has a markedly higher choleretic activity than catechin and furthermore the choleretic effect is of longer duration.

2. Choleretic Activity—Intra-Peritoneal Administration

The choleretic activities of catechin and catechin pentacetyl ferulate were determined in the manner described in paragraph A above.

From the results shown in Table 2 it can be seen that catechin pentacetyl ferulate has a marked choleretic action when administered orally as determined by measurement of bile volume and the dry residue content thereof three hours after treatment, while catechin displays no statistically significant choleretic effect.

3. Hypolipaemic Effect—Effect on Olive Oil-Induced Hyperlipaemia

The hypolipaemic activity of catechin and epicatechin was determined in the manner described in paragraph B1 above.

As can be seen from the results given in Table 3, epicatechin has a marked hypolipaemic effect, whereas catechin has no statistically significant hypolipaemic effect when administered under similar conditions.

| D. Toxicity | |
| --- | --- |
| Catechin | $LD_{50} > 2000$ mg/kg per os |
| | $LD_{50} > 1000$ mg/kg i.p. |
| Catechin pentacetylferulate | $LD_{50} > 1000$ mg/kg i.p. |

The following formulations exemplify pharmaceutical compositions according to the invention:

| | | |
| --- | --- | --- |
| 1. | Sugar Coated Tablets | |
| | Catechin peracetylferulate | 150 mg |
| | Excipients (corn starch, lactose, talc, magnesium stearate, sodium alginate, sugar, Gum arabic, magnesium carbonate) q.s. | 450 mg |
| 2. | Tablets | |
| | Epicatechin | 200 mg |
| | Excipients (starch, lactose) q.s. | 400 mg |
| 3. | Capsules | |
| | Epicatechin | 200 mg |
| | Excipients (lactose, magnesium stearate) q.s. | 250 mg |
| 4. | Soft Gelatine Capsules | |
| | Catechin peracetylferulate | 200 mg |
| | Excipients (vegetable oil, hyrogenated (vegetable oils, beeswax, soya lecithin, coating soft gelatin) q.s. | 500 mg |
| 5. | Syrup | |
| | Epicatechin | 2 g |
| | Excipients (propylene glycol, polyethylene glycol 400, soya lecithin, carboxy vinyl polymer, triethanolamine, purified water) q.s. | 100 g |

TABLE 1

| | CHOLERETIC ACTION IN THE AWAKE RAT | | | | | |
|---|---|---|---|---|---|---|
| | Bile Volume (ml) | | | uz,35/58 Dry Residue (mg) | | |
| Treatment | Before Treatment | 2 Hours after Treatment | 3 Hours after Treatment | Before Treatment | 2 Hours after Treatment | 3 Hours after Treatment |
| Catechin 200 mg/kg per os | 0.79 ± 0.02 | 0.84 ± 0.02 (+ 13) | 0.81 ± 0.03 | 16.0 ± 0.60 | 18.2 ± 0.37* (+ 21) | 16.6 ± 0.81 |
| Epicatechin 200 mg/kg per os | 0.65 ± 0.07 | 1.02 ± 0.07 (+ 59) | 0.89 ± 0.09* (+ 39) | 12.4 ± 1.81 | 18.1 ± 2.0* (+ 46) | 16.5 ± 2.13* (+ 33) |

*Significantly different (P>0.05) from the mean value before treatment according to Students "t" test. The figures in brackets indicate the percentage increase compared with the value before treatment.

TABLE 2

| | CHOLERETIC ACTION IN THE AWAKE RAT | | | |
|---|---|---|---|---|
| | Bile Volume (ml) | | Dry Residue (mg) | |
| Treatment | Before Treatment | 3 Hours after Treatment | Before Treatment | 3 Hours after Treatment |
| Catechin 100 mg/kg i.p. | 0.54 ± 0.11 | 0.62 ± 0.08 (+ 15) | 8.0 ± 1.60 | 10.0 ± 4.20 (+ 25) |
| Catechin pentacetylferulate 100 mg/kg i.p. | 0.53 ± 0.06 | 0.88 ± 0.05 (+ 66) | 11.5 + 1.10 | 15.6 ± 0.60 (+ 36) |

*Significantly different (P<0.05) from the mean value before treatment according to Student's "t" test. The figures in brackets indicate the percentage increase compared with the value before treatment.

TABLE 3

| EFFECT ON OLIVE OIL-INDUCED HYPERLIPAEMIA | | | |
|---|---|---|---|
| Treatment | Dose mg/kg per os | No. of Animals | Triglycerides mg/100 ml |
| Controls (water) | — | 18 | 171.5±18.6 |
| Catechin | 100 | 18 | 120.7±17.6 (− 30) |
| Epicatechin | 100 | 18 | 98.6±12.0* (− 42) |

*Significantly different (P<0.02) from the mean value of the controls according to Student's "t" test. The figures in brackets indicate the percentage reduction compared with the controls.

We claim:

1. A pharmaceutical composition for inducing a choleretic effect, comprising a pharmaceutically acceptable diluent or carrier and as active ingredient a choleretic effect-inducing amount of a compound selected from the group consisting of epicatechin, catechin pentacaffeate, catechin penta (acetylferulate), epicatechin penta (acetylferulate) and catechin penta 2-(p-chlorophenoxy)-2-methyl propionate.

2. A pharmaceutical composition for treatment of hyperlipaemia or hypercholesterolaemia, comprising a pharmaceutically acceptable diluent or carrier and as active ingredient an anti-hyperlipaemic or antihypercholesterolaemic effective amount of a compound selected from the group consisting of epicatechin, catechin pentacaffeate, catechin penta (acetylferulate), epicatechin penta(acetylferulate) and catechin penta 2-(p-chlorophenoxy)-2-methyl propionate.

3. A method inducing a choleretic effect in an animal which comprises administering to said animal a choleretic effect-inducing effective amount of a compound selected from the group consisting of epicatechin, catechin pentacaffeate, catechin penta(acetyl ferulate), epicatechin penta (acetylferulate) and catechin penta 2-(p-chlorophenoxy)-2-methyl propionate.

4. A method of inducing a hypolipaemic or hypocholesterolaemic effect in an animal which comprises administering to said animal an anti-hyperlipaemic or anti-hypercholesterolaemic effective amount of a compound selected from the group consisting of epicatechin, catechin pentacaffeate, catechin penta (acetyferulate), epicatechin penta (acetylferulate) and catechin penta 2-(p-chlorophenoxy)-2-methyl propionate as active ingredient.

5. A pharmaceutical composition for inducing a hepatoprotective effect, comprising a pharmaceutically acceptable diluent or carrier and as active ingredient a hepatoprotective effective amount of a compound selected from the group consisting of epicatechin, catechin pentacaffeate, catechin penta (acetylferulate), epicatechin penta (acetylferulate) and catechin penta 2-(p-chlorophenoxy)-2-methyl propionate.

6. A method of inducing a hepatoprotective effect in an animal which comprises administering to said animal a hepatoprotective effective amount of a compound selected from the group consisting of epicatechin, catechin pentacaffeate, catechin penta (acetylferulate), epicatechin penta (acetylferulate) and catechin penta 2-(p-chlorophenoxy)-2-methyl propionate.

7. Catechin pentacaffeate.

8. Catechin penta(acetylferulate).

9. Epicatechin penta(acetylferulate).

10. Catechin penta 2-(p-chlorophenoxy)-2-methyl propionate.

* * * * *